(12) United States Patent
Fujita et al.

(10) Patent No.: US 8,272,518 B2
(45) Date of Patent: Sep. 25, 2012

(54) DIRECT HEMOPERFUSION ADSORBER PACKED WITH ADSORBENT HAVING WATER INSOLUBLE MICROPARTICLE REMOVED THEREFROM, AND METHOD OF OBTAINING DIRECT HEMOPERFUSION ADSORBENT HAVING WATER INSOLUBLE MICROPARTICLE REMOVED THEREFROM

(75) Inventors: Koji Fujita, Osaka (JP); Masaru Nakatani, Osaka (JP); Akira Kobayashi, Osaka (JP); Takehiro Nishimoto, Osaka (JP)

(73) Assignee: Kaneka Corporation, Osaka (JP)

( * ) Notice: Subject to any disclaimer, the term of this patent is extended or adjusted under 35 U.S.C. 154(b) by 1080 days.

(21) Appl. No.: 11/572,542

(22) PCT Filed: Jul. 20, 2005

(86) PCT No.: PCT/JP2005/013328
§ 371 (c)(1),
(2), (4) Date: Aug. 11, 2008

(87) PCT Pub. No.: WO2006/009179
PCT Pub. Date: Jan. 26, 2006

(65) Prior Publication Data
US 2008/0314817 A1     Dec. 25, 2008

(30) Foreign Application Priority Data
Jul. 23, 2004   (JP) .................................. 2004-215411

(51) Int. Cl.
*B01D 24/10*   (2006.01)
*B01D 24/12*   (2006.01)
*B01D 39/00*   (2006.01)

(52) U.S. Cl. ..................... 210/503; 210/502.1; 210/505; 210/510.1

(58) Field of Classification Search ............... 210/502.1, 210/503, 505, 510.1
See application file for complete search history.

(56) References Cited

U.S. PATENT DOCUMENTS
4,171,283 A    10/1979    Nakashima et al.
(Continued)

FOREIGN PATENT DOCUMENTS
EP      1356832 A1    10/2003
(Continued)

OTHER PUBLICATIONS
Extended European Search Report for counterpart European Application No. 05766271.0 dated Oct. 6, 2010.
(Continued)

*Primary Examiner* — John Kim
(74) *Attorney, Agent, or Firm* — Connolly Bove Lodge & Hutz LLP

(57) ABSTRACT

The present invention has its object to provide a direct hemoperfusion adsorber packed with an adsorbent made by using a water-insoluble carrier having a relatively readily available particle size distribution, with water-insoluble microparticles having been removed therefrom, without needing any special granulation apparatus or coating apparatus, and method of obtaining a direct hemoperfusion adsorbent having water-insoluble microparticles removed therefrom.

Now, a direct hemoperfusion adsorber has been obtained that is packed with an adsorbent having a number average particle diameter of not smaller than 300 µm but not larger than 600 µm, with the coefficient of variance in particle diameter distribution being not lower than 10% but not higher than 20%, and having water-insoluble microparticles removed therefrom to a safe level, without the loss of the adsorbent, by using a water-insoluble microparticle-removing-mesh such that the ratio of the mesh opening size for removing water-insoluble microparticles to the mesh opening size of the adsorber is not lower than 1.3 but not higher than 1.5.

1 Claim, 2 Drawing Sheets

U.S. PATENT DOCUMENTS

| | | | |
|---|---|---|---|
| 4,358,376 A | 11/1982 | Moriuchi et al. | |
| 4,654,420 A * | 3/1987 | Furuyoshi et al. | 536/59 |
| 4,694,044 A * | 9/1987 | Kiniwa | 525/178 |
| 2004/0222144 A1 * | 11/2004 | Nakatani et al. | 210/435 |

FOREIGN PATENT DOCUMENTS

| | | |
|---|---|---|
| JP | 56-62540 A | 5/1981 |
| JP | 57-43747 A | 3/1982 |
| JP | 62-191033 A | 8/1987 |
| JP | 1-275601 A | 11/1989 |
| JP | 4-145941 A | 5/1992 |
| JP | 7-136256 | 5/1995 |
| JP | 2001-204816 A | 7/2001 |
| WO | 02/060512 A1 | 8/2002 |

OTHER PUBLICATIONS

International Preliminary Report on Patentability for PCT/JP2005/013328.

* cited by examiner

DIRECT HEMOPERFUSION ADSORBER PACKED WITH ADSORBENT HAVING WATER INSOLUBLE MICROPARTICLE REMOVED THEREFROM, AND METHOD OF OBTAINING DIRECT HEMOPERFUSION ADSORBENT HAVING WATER INSOLUBLE MICROPARTICLE REMOVED THEREFROM

CROSS-REFERENCE TO RELATED APPLICATIONS

This application is a National Stage of PCT/JP2005/013328 filed Jul. 20, 2005 which in turn claims priority from Japanese Application 2004-215411, filed Jul. 23, 2004 disclosures of which are incorporated herein by reference.

TECHNICAL FIELD

The present invention relates to a direct hemoperfusion adsorber packed with an adsorbent having a number average particle diameter of not smaller than 300 μm but not larger than 600 μm, with the coefficient of variance in particle diameter distribution being not lower than 10% but not higher than 20%, and having water-insoluble microparticles removed therefrom, and to a method of obtaining direct hemoperfusion adsorbents having water-insoluble microparticles removed therefrom.

BACKGROUND ART

Adsorptive blood purification therapy consisting in positively removing, from the blood of patients, pathogenic substances occurring therein has been attempted energetically and has been found effective against a number of intractable diseases. Two techniques are available for adsorptive blood purification therapy, namely plasma perfusion and direct hemoperfusion. The plasma perfusion technique is a two-step system comprising plasma separation means and blood purification means and thus requires an apparatus to serve exclusively for safe operation, hence the treatment cost goes up and a complicated operation is required. On the other hand, the direct hemoperfusion technique is a one-step system in which the blood is directly perfused through an adsorber; therefore, the operation is simple and easy, and the amount of the extracorporeally circulated blood is small, so that the load on patients can be reduced. However, one of the problems encountered by the adsorber for direct hemoperfusion is the occurrence of water-insoluble microparticles in the adsorber.

Water-insoluble microparticles are mainly of adsorbent origin and, theoretically, can flow out from the adsorbent and enter the human body on the occasion of treatment by direct hemoperfusion. In case where water-insoluble microparticles enter the body in large amounts, such serious safety problems as vascular occlusion and accumulation in organs are anticipated.

Typical examples of the direct hemoperfusion adsorber which are currently available on the market are the following (cf. Non-Patent Document 1).

One is KANEKA CORPORATION's adsorber for removing β2 microglobulin (molecular weight: about 12,000). The adsorbent (cf. Non-Patent Document 2) used in this adsorber has a particle diameter of about 500 μm with a uniform particle diameter distribution. As for the intended use, the adsorber is applied in the treatment of amyloidosis accompanied by arthralgia and utilized on the occasion of hemodialysis. Since the adsorbent is uniform in particle diameter distribution, it is easy to remove water-insoluble microparticles without the loss of the adsorbent by using a device for removing water-insoluble microparticles (cf. Patent Document 1), for instance. Thus, the use of such an adsorbent uniform in particle diameter distribution is a measure against water-insoluble microparticles. However, a special granulation apparatus (cf. Patent Document 3) is required for the production of an adsorbent uniform in particle diameter distribution (cf. Patent Document 2). The actual situation is that any general-purpose water-insoluble carrier uniform in particle diameter distribution and capable of being applied as an adsorbent carrier is not commercially available.

Another one is KURARAY MEDICAL, INC.'s kidney-assisting adsorptive blood purifier. The adsorbent (cf. Non-Patent Document 2) used in this adsorber is 400 to 900 μm in particle diameter and is used as a kidney assistant for removing uremia-causing substances (molecular weight: about 100 to 2,000). For use in direct hemoperfusion adsorbent, active carbon is surface-coated with poly(hydroxyethyl methacrylate) so that water-insoluble microparticles may not be released. That is, the adsorbent has a coating as a measure against water-insoluble microparticles. However, it is necessary to provide the adsorbent with a coating, so that the production process becomes complicated.

As explained above, these adsorbers are produced, for use in direct hemoperfusion, by particular processes considering the water-insoluble microparticle-related safety problem. Due to the necessity of those particular processes, the production costs of products inevitably increase. Accordingly, a direct hemoperfusion adsorber that can be obtained in a simple and easy manner using a general-purpose water-insoluble carrier, for instance, without requiring any special granulation apparatus or coating apparatus is desired.

A patent specification has so far been laid open concerning the removal of water-insoluble microparticles from an adsorbent for medical use (cf. Patent Document 1). However, the technology disclosed therein is characterized by using a plurality of circulation and microparticle removal lines. The specification neither describes the particle diameter distribution of the adsorbent from which water-insoluble microparticles are to be removed nor specifies the ratio of the mesh opening size for removing water-insoluble microparticles to the mesh opening size of the adsorber.

Patent Document 1: Japanese Kokai Publication Hei-04-145941
Patent Document 2: Japanese Kokai Publication Hei-01-275601
Patent Document 3: Japanese Kokai Publication Sho-62-191033
Non-Patent Document 1: Japan Medical Devices Manufacturers Association: Specified Health Insurance Medical Materials Guidebook, pp. 175-, 2003
Non-Patent Document 2: Zinko Zoki (Japanese Journal of Artificial Organs), Vol. 23, No. 2, pp. 439-, 1994
Non-Patent Document 3: Kagaku Kogaku (Chemical Engineering of Japan), Vol. 50, No. 10, pp. 685-, 1986)

SUMMARY OF THE INVENTION

The present invention is to provide a direct hemoperfusion adsorber packed with an adsorbent made by using a water-insoluble carrier having a relatively readily available particle size distribution (with a number average particle diameter of not smaller than 300 μm but not larger than 600 μm, with the coefficient of variance in particle diameter distribution being not lower than 10% but not higher than 20%), with water-insoluble microparticles having been removed therefrom, without needing any special granulation apparatus or coating apparatus, and a method of obtaining direct hemoperfusion adsorbents having water-insoluble microparticles removed therefrom.

The present inventors made intensive investigations to obtain a direct hemoperfusion adsorber packed with an adsorbent made by using a water-insoluble carrier having a relatively readily available particle size distribution, with water-insoluble microparticles having been removed therefrom, without needing any special granulation apparatus or coating apparatus. As a result, they have now invented a direct hemoperfusion adsorber packed with an adsorbent having water-insoluble microparticles removed therefrom to a therapeutically safe level without the loss of the adsorbent in removing water-insoluble microparticles.

Thus, the present invention relates to a direct hemoperfusion adsorber packed with an adsorbent comprising a group of water-insoluble carrier particles having a number average particle diameter of not smaller than 300 μm but not larger than 600 μm, with the coefficient of variance in particle diameter distribution being not lower than 10% but not higher than 20%, wherein the average measured value of the number of water-insoluble microparticles not smaller than 10 μm as occurring in the adsorber+6SD is not larger than 24,000 per adsorber and the average measured value of the number of water-insoluble microparticles greater than 25 μm+6SD is not greater than 4,000 per adsorber.

The invention also relates to a method of obtaining adsorbents for packing in direct hemoperfusion adsorbers which comprises removing water-insoluble microparticles from an adsorbent comprising a group of particles having a number average particle diameter of not smaller than 300 μm but not greater than 600 μm, with the coefficient of variation in particle diameter distribution being not lower than 10% but not higher than 20%, by using a mesh such that the ratio of the mesh opening size for removing water-insoluble microparticles to the mesh opening size of the adsorber is not lower than 1.3 but not higher than 1.5.

(Effect of the Invention)

In accordance with the invention, it is now possible to obtain direct hemoperfusion adsorbers packed with an adsorbent made by using a water-insoluble carrier having a relatively readily available particle size distribution, with water-insoluble microparticles having been removed therefrom to a therapeutically safe level, without needing any special granulation apparatus for producing an adsorbent uniform in particle diameter distribution from which water-insoluble microparticles can be readily removed or without need of any coating treatment for inhibiting the release of water-insoluble microparticles. In accordance with the invention, it is also possible to obtain direct hemoperfusion adsorbers with ease and increase the safety against water-insoluble microparticles on the occasion of treatment by using the same.

EXPLANATION OF SYMBOLS

| | |
|---|---|
| 1 | Adsorbent |
| 2 | water-insoluble microparticle |
| 3 | mesh for removing water-insoluble microparticles |
| 4 | filter |
| 5 | pump |
| 6 | nozzle |
| 7 | microparticle removing vessel |
| 8 | blood inlet |
| 9 | blood outlet |
| 10 | column |
| 11 | adsorber |
| 12 | adsorber mesh. |

DETAILED DESCRIPTION OF THE INVENTION

Hereinafter, typical examples of the mode of embodiment of the invention are described.

The adsorbent to be used in the practice of the invention is not particularly restricted but may be any one showing affinity for pathogenic substances. As an example, there may be mentioned an adsorbent derived from a water-insoluble carrier by immobilizing a ligand showing affinity for a pathogenic substance thereon.

The water-insoluble carrier to be used in the practice of the invention is a solid at ordinary temperature and ordinary pressure and is insoluble in water and has pores appropriate in size, namely has a porous structure. The shape of the water-insoluble carrier to be used is spherical or granular. Thus, use may be made of general-purpose carriers conventionally used as gel filtration materials, raw materials of ion exchangers, affinity chromatography carriers, polymer carriers, body fluid purification carriers, cosmetic additives and so forth.

When a spherical or granular water-insoluble carrier is used in a direct hemoperfusion system, it is necessary for the particle diameter to be larger as compared with the case of passing a liquid component such as plasma (plasma perfusion) so that channels allowing the passage of blood cells or the like may be secured. However, as the particle diameter increases, the lengths of diffusion of pathogenic substances to be adsorbed increase and the dynamic adsorption efficiency decreases. Thus, the treatment time is prolonged. The adsorbent to be used in the practice of the invention preferably has an average particle diameter of not smaller than 300 μm but not larger than 600 μm, more preferably not smaller than 400 μm but not larger than 500 μm, so that smooth blood passage and good adsorption efficiency may be achieved in direct hemoperfusion.

The particle diameter distribution of the water-insoluble carrier is preferably as uniform as possible in a direct hemoperfusion system from the blood passage viewpoint. However, for obtaining a highly uniform one, the granulation process becomes difficult and a special apparatus is required. On the other hand, when the particle diameter distribution is broad, the adsorbent is so closely packed that the blood channels become narrow, hence the passage of blood becomes difficult. In the case of a broad particle diameter distribution, the loss of the adsorbent also increases on the occasion of removing water-insoluble microparticles as the removal treatment proceeds.

Usable as the adsorbent in the practice of the invention are, among others, general-purpose water-insoluble carriers having a particle diameter distribution readily obtainable without needing any special granulation apparatus. Actually, the coefficient of variance in particle diameter distribution (standard deviation/average particle diameter×100 for a sample as calculated on the number of particles basis) is preferably not lower than 10% but not higher than 20%. The average particle diameter and the coefficient of variance in particle diameter distribution of the adsorbent are determined by diameter measurement of 100 or more individual particles on an enlarged photograph of the adsorbent as taken under a stereomicroscope, for instance, followed by calculation based on the number of particles.

As for the strength of the water-insoluble carrier to be used in the practice of the invention, an excessively soft one or a readily breakable one is undesirable. Once compaction occurs as a result of blood passage, no more sufficient blood flow can be obtained and the continued treatment may become impossible, to say nothing of prolonging the period of treatment. For preventing adsorbent compaction, the adsorbent is preferably one having a sufficient mechanical strength (hard one). The term "hard one" as used herein refers to one such that when the adsorbent is uniformly packed in a cylindrical column and an aqueous liquid is passed therethrough, the relation between pressure loss and flow rate is linear at least until 0.3 kgf/cm$^2$, as shown later herein in a reference example. Water-insoluble carriers continuously releasing water-insoluble microparticles during transfer and packing and in various steps are undesirable.

The material of the water-insoluble carrier to be used in the practice of the invention is not particularly restricted but there may be mentioned, as typical examples, organic carriers made of cellulose, cellulose acetate, chitin, chitosan, dextrin, agarose or a like polysaccharide, and synthetic polymers such as polystyrene, styrene-divinylbenzene copolymers, polyacrylamide, polyacrylic acid, polymethacrylic acid, polyacrylic esters, polymethacrylic esters and polyvinyl alcohol, etc. The carrier may have a coating layer made of a hydroxy group-containing polymer material such as poly(hydroxyethyl methacrylate) or a graft copolymer such as a copolymer of a polyethylene oxide chain-containing monomer and another polymerizable monomer, for instance, although such coating is not essential. Such inorganic materials as glass, alumina or ceramics may also be utilized. Among those, cellulose and a synthetic polymer comprising polyvinyl alcohol, for instance, are preferably used from the practical viewpoint since an active group can easily be introduced onto the carrier surface.

Among them, carriers made of cellulose are most preferably used. Such cellulose carriers are relatively high in mechanical strength and tough, so that they are hardly destructed and hardly release water-insoluble microparticles and, when they are packed in adsorbers, they hardly compact even upon passage of blood at high rates, so that blood can be passed therethrough at high rates. Further, they are superior to synthetic polymer carriers, for example higher in safety, and can be most suitably used as water-insoluble carriers in the practice of the invention.

As examples of the pathogenic substances to be described in the invention, there may be mentioned low-density lipoproteins, very low-density lipoproteins and like lipoproteins occurring in body fluids and causing arteriosclerosis, immunoglobulins (A, D, E, G, M), anti-DNA antibodies, anti-acetylcholine receptor antibodies, anti-blood type antibodies, anti-platelet antibodies and other autoantibodies and antigen-antibody complexes, endotoxins, rheumatoid factors, macrophages and cancer tissue infiltrating T cells, among others.

In the practice of the invention, the substance showing affinity for pathogenic substances is not particularly restricted but may be any substance capable of adsorbing the target pathogenic substances. The affinity between a substance showing affinity for a pathogenic substance and the pathogenic substance includes a biological interaction-based one and a physicochemical interaction-based one. As ones utilizing a biological interaction, there may be mentioned ones with an antigen immobilized thereon, ones with an antibody immobilized thereon, and substances showing affinity for a pathogenic substance(s) under utilization of complement fixation, Fc bonding or some other biological interaction. As ones for utilizing a physical interaction, there are substances showing affinity for a pathogenic substance(s) under utilization of an electrostatic interaction or a hydrophobic interaction.

In the case of adsorption of low-density lipoproteins, substances showing affinity for negative group-containing pathogenic substances can be used as typical examples of the substance showing affinity for pathogenic substance(s) under utilization of a physicochemical interaction. As examples of the substance showing affinity for negative group-containing pathogenic substances, there may be mentioned dextran sulfate, heparin, chondroitin sulfate, chondroitin polysulfate, haparitin sulfate, xylan sulfate, charonin sulfuric acid, cellulose sulfate, chitin sulfate, chitosan sulfate, pectin sulfate, inulin sulfate, arginine sulfate, glycogen sulfate, polylactose sulfate, carrageenin sulfate, starch sulfate, polyglucose sulfate, laminarin sulfate, galactan sulfate, levan sulfate, mepesulfate and like sulfated polysaccharides, phosphotungstic acid, poly(sulfated anethole), polyvinyl alcohol sulfate, polyphosphoric acid, polyacrylic acid and so forth. Among these, sulfated polysaccharides, in particular, are highly effective. Heparin and dextran sulfate may be mentioned as examples preferred from the clinical practice viewpoint.

In the case of adsorption of fibrinogen, tryptophan derivatives, which are hydrophobic amino acids, can be used as typical examples of the substance showing affinity for a pathogenic substance(s) under utilization of a hydrophobic interaction. The tryptophan derivatives include tryptophan, tryptophan esters such as tryptophan ethyl ester and tryptophan methyl ester, and compounds having an indole ring-containing tryptophan-like structure, for example tryptamine and tryptophanol. These tryptophan derivatives may be in the L form, D form or DL form or in the form of a mixture of these forms. Mixtures of two or more tryptophan derivatives may also be used. Among these tryptophan derivatives, tryptophan is preferred from the safety viewpoint and, in particular, L-tryptophan, which is a naturally occurring amino acid, of which safety data are available abundantly and which is readily available at low cost, is most preferably used from the practical viewpoint.

In view of the above-given examples of the substance showing affinity for pathogenic substances having a negative group and/or a hydrophobic group, any substance that has affinity for various pathogenic substances showing interaction therewith can be used according to the pathogenic substance to be adsorbed. A plurality of substances showing affinity for such pathogenic substances as mentioned above may be immobilized. In a typical example, it is possible, for simultaneous adsorption of low-density lipoproteins and fibrinogen, to select dextran sulfate and a tryptophan derivative simultaneously as substances showing affinity for such pathogenic substances.

Available as the method of immobilizing a substance showing affinity for a pathogenic substance(s) onto a water-insoluble carrier in the practice of the invention are methods known in the art which utilize convalent bonding, ionic bonding, physical adsorption, embedding, or precipitation/insolubilization to the surface, for instance. An appropriate method can be selected from among them according to the substance showing affinity for the pathogenic substance and the water-insoluble carrier material. Considering the elution of the substance showing affinity for a pathogenic substance(s) during sterilization, immobilization/insolubilization by covalent bonding is preferred. A spacer may be inserted between the water-insoluble carrier and the substance showing affinity for a pathogenic substance(s) according to need.

Known as the method of improving the reactivity of a water-insoluble carrier with a substance showing affinity for a pathogenic substance(s) on the occasion of immobilization of the substance showing affinity for a pathogenic substance(s) onto the water-insoluble carrier through covalent bonding are the cyanogens halide method, epichlorohydrin method, bisepoxide method and bromoacetyl bromide method, among others. By these methods, a functional group such as an amino, carboxyl, hydroxyl, thiol, acid anhydride, succinylimide, chlorine, aldehyde, epoxy or tresyl group is introduced into the water-insoluble carrier. A particularly preferred example among these groups is an epoxy group derived by the epichlorohydrin method in view of the stability on the occasion of autoclaving.

In the practice of the invention, the exclusion limit of molecular weight of the water-insoluble carrier for spherical proteins should be greater than the molecular weight of the pathogenic substance to be removed and preferably is $2 \times 10^4$ or higher. The exclusion limit of molecular weight is the molecular weight of those molecules which have the minimum molecular weight among molecules incapable of entering pores (capable of being excluded) when a sample comprising molecules differing in molecular weight is passed through the carrier in size exclusion chromatography, as described in a monograph (Sadao Mori: Size Exclusion Chromatography, published by KYORITSU SHUPPAN CO., LTD.). More specifically, when the exclusion limit of molecular weight for spherical proteins is below $5 \times 10^5$ in the case of the pathogenic substances to be adsorbed being low-density lipoproteins and fibrinogen, for instance, the carrier is insufficient in adsorptive activity against fibrinogen and low-density lipoproteins, hence is not suited for practical use. When the exclusion limit of molecular weight for spherical proteins is higher than $1 \times 10^8$, the pore size is too large and the surface area contributing to adsorption becomes decreased, with the result that the adsorptive activity against fibrinogen and low-density lipoproteins becomes small. In view of the foregoing, the water-insoluble carrier to be used in the practice of the invention preferably has an exclusion limit of molecular weight for spherical proteins of not lower than $5 \times 10^5$ but not higher than $1 \times 10^8$; from the adsorptive activity performance viewpoint, it is more preferably not lower than $1 \times 10^6$ but not higher than $1 \times 10^8$, still more preferably not lower than $2 \times 10^6$ but not higher than $1 \times 10^8$.

The adsorber according to the invention comprises a column having a blood flow inlet and a blood flow outlet, each equipped with a mesh allowing the passage of blood containing hemocyte components but not allowing the passage of the adsorbent, and packed with the adsorbent of the invention. The capacity of the adsorber of the invention is required to be not smaller than 100 mL so that the pathogenic substance concentration in blood may be reduced. From the adsorption performance viewpoint, there is not limitation to the volume of the adsorber. Since, however, there arises the fear of hypotension when an excessively large amount of blood is taken out of the body, the adsorber capacity is preferably not greater than 600 mL. Further, from the viewpoint that even when incorporated into a circuit for another blood purification therapy such as hemodialysis, such adsorber will never excessively increase the extracorporeal blood circulation and the possibility of hypotension possibly resulting from extracorporeal blood circulation may be reduced as far as possible, the adsorber capacity is preferably not larger than 400 mL.

Since the adsorber of the invention is used in direct hemoperfusion, which is simple and easy in practice, the mesh thereof should have a mesh opening size such that the mesh will neither allow the adsorbent to flow out of the adsorber nor capture hemocyte components. If the adsorber is equipped with a mesh whose opening size is smaller than hemocyte components, hemocyte components will be captured by the adsorber. Conversely, if the adsorber is equipped with a mesh whose opening size is greater than the adsorbent, the adsorbent in the adsorber will flow out into the circulating blood and then enter the body. Therefore, the adsorber mesh opening size is preferably not smaller than 100 μm but not larger than 200 μm.

The "water-insoluble microparticles" so referred to herein are water-insoluble microparticles capable of flowing out of the adsorber and entering the body without being captured by the adsorber mesh during treatment. Therefore, the upper limit to the diameters of the particles defined as such water-insoluble microparticles depends on the mesh opening size of the adsorber. When the adsorber mesh opening size is 150 μm, for instance, the upper limit to the water-insoluble microparticle diameters is 150 μm.

The occurrence, within the adsorber, of water-insoluble microparticles of a size allowing their flowing out of the adsorber is a great problem from the safety viewpoint. According to the criterion for water-insoluble microparticles in injections (not smaller than 100 mL in volume) as described in the "Methods of testing for water-insoluble microparticles" in the "Japanese Pharmacopoeia, 14th Revised Edition, General Rules for Preparations, 17 Injections", a standard of safety for water-insoluble microparticles in a direct hemoperfusion adsorber may be considered as follows.

Two relevant methods are described in the Pharmacopoeia. According to the second method "Method using a microscope", which imposes a stricter limit than the first method "Method using a light-shielded automatic microparticle measuring apparatus", the standard for the number of water-insoluble microparticles is that the number of microparticles not smaller than 10 μm should be not greater than 12 and the number of microparticles not smaller than 25 μm should be not greater than 2 in each milliliter of an injection (not smaller than 100 mL in volume). Although, in some instances, an injection is injected, as a replenisher solution, into the vein in amounts as large as 15 to 18 L during hemofiltration, the total amount of a transfusion used in fluid therapy is generally not larger than 2 to 2.5 L per day, as described in a monograph (Tateki Kitamura: Zuhyo Yueki Manyuaru (Manual of Transfusions in form of charts), published by Chugai Igakusha). Supposing here that the total volume of a transfusion is 2 L and that even when all the water-insoluble microparticles in the adsorber the number of which corresponds to the maximum value allowed to be contained in that transfusion enter the human body during treatment, his or her safety is secured, the measure of safety concerning the number of water-insoluble microparticles will be such that the number of water-insoluble microparticles not smaller than 10 μm should be not greater than 24,000 per adsorber and the number of water-insoluble microparticles not smaller than 25 μm should be not greater than 4,000 per adsorber. Therefore, when the variation in the number of water-insoluble microparticles among individual adsorbers is taken into consideration, the measure of safety concerning the number of water-insoluble microparticles will be such that the mean of measured values of water-insoluble microparticles not smaller than 10 μm+6SD should be not greater than 24,000 per adsorber and the mean of measured values of water-insoluble microparticles not smaller than 25 μm+6SD should be not greater than 4,000 per adsorber. In the practice of the invention, the mean of measured values of water-insoluble microparticles and the SD are the number-based mean of measured values of water-insoluble microparticles and the standard deviation as calculated from the respective measured number values for 6 adsorbers. "6SD" is the value 6-times the standard deviation. In the practice of the invention, the number of water-insoluble microparticles is measured by the second method "Method using a microscope" described above. It is also possible to count that number using a Coulter counter (measuring the equivolume sphere equivalent diameter of a particle passing through an aperture by detecting the electric resistance on the occasion of the passage).

In the practice of the invention, the number of water-insoluble microparticles is determined in the following manner. While water filtered through a 0.22-μm filter is passed through an adsorber packed with an adsorbent, the adsorbent is discharged into a vessel incapable of releasing any water-insoluble microparticles (e.g. commercially available vacant container for physiological saline), the whole amount of the contents in the vessel is transferred to another prepared vessel. This transfer procedure between the two vessels is repeated 5 times and, after thorough stirring of the adsorbent, the vessel contents are allowed to stand until precipitation of the adsorbent. Upon precipitation of the adsorbent, the supernatant is sampled and the concentration of microparticles in the supernatant is determined by the measurement method mentioned above. Based on the thus-measured microparticle concentration value, the number of water-insoluble microparticles per adsorber is determined by calculating the number of water-insoluble microparticles contained in the adsorber.

Figure 1:
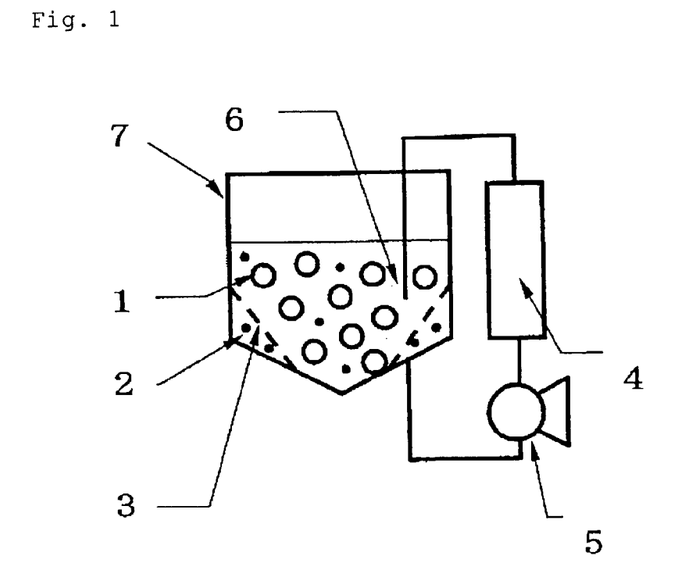
FIG. 1 This figure schematically shows the removal of microparticles.

The removal of water-insoluble microparticles can be effected by a batch procedure, such as decantation, as well. However, this requires time and is inefficient. Thus, it is preferable that water-insoluble microparticles can be removed continuously, for example in the following manner. An apparatus for removing water-insoluble microparticles in the practice of the invention is schematically shown in FIG. 1 by way of example. In FIG. 1, the reference numeral 1 denotes an adsorbent, 2—each water-insoluble microparticle, 3—a mesh for removing microparticles, 4—a filter, 5—a pump, 6—a nozzle, and 7—a microparticle removing vessel. The adsorbent is dispersed in a washing liquid in a container equipped with the mesh allowing the passage of water-insoluble microparticles but not allowing the passage of the adsorbent, and the washing liquid is circulated from the section separated by the mesh and free of the adsorbent to the container through the nozzle using a circulating and water-insoluble microparticle removing line equipped with the filter for capturing water-insoluble microparticles while causing the water-insoluble microparticles in the washing liquid to be captured by the filter. Thus, the water-insoluble microparticles are removed while the adsorbent is always dispersed in the microparticle removing vessel.

FIG. 1 shows only one example. Any apparatus having a mesh for removing water-insoluble microparticles can be used without any particular restriction. The apparatus may have a plurality of water-insoluble microparticle-removing lines.

If the mesh opening size for removing water-insoluble microparticles is too small, it will become impossible to remove water-insoluble microparticles and, if it is excessively large, the adsorbent partly flows out during removal of water-insoluble microparticles, resulting in an adsorbent loss. Further, when the amount of the adsorbent having flown out through the mesh is large, the filter for removing water-insoluble microparticles will get blocked, making it difficult to carry out the treatment continuously. The mesh opening size for removing water-insoluble microparticles is preferably such that the ratio between the mesh opening size for removing water-insoluble microparticles and the mesh opening size of the adsorber is not lower than 1.3 but not higher than 1.5.

Figure 2:
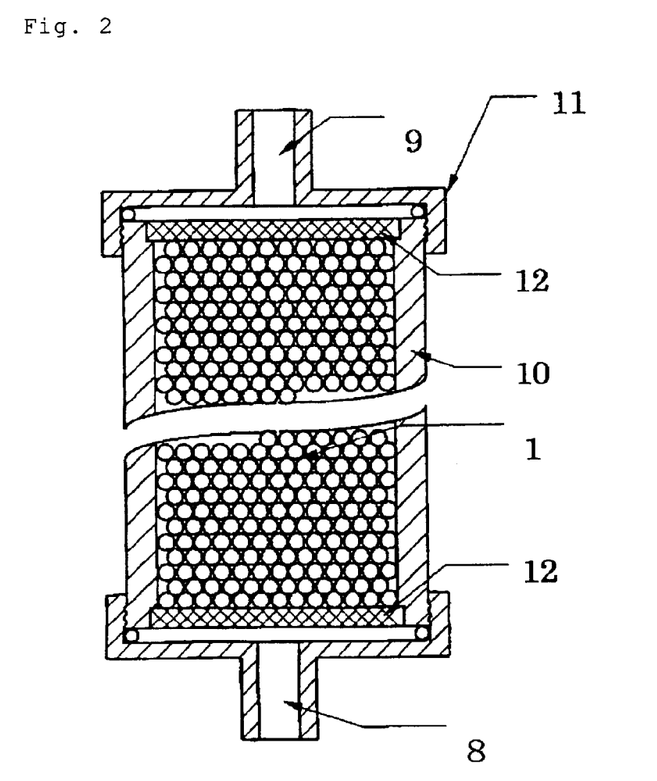
FIG. 2 This figure illustrates an adsorber.

Now, an example of the adsorber of the invention is schematically shown, in cross section, in FIG. 2.

In FIG. 2, the reference numeral 1 denotes an adsorbent, 8—a blood inlet, 9—a blood outlet, 10—a column, 12—an adsorber mesh, and 11—an adsorber. The adsorber of the invention, however, is not limited to such a specific example. Morphologically, the adsorber is not particularly restricted provided that it comprises container having a liquid inlet and a liquid outlet and equipped with means for inhibiting adsorbent discharging out of the container and is packed with an adsorbent capable of adsorbing a pathogenic substance(s).

BEST MODE FOR CARRYING OUT THE INVENTION

The following examples illustrate the invention more specifically.

Reference Example

A cylindrical glass column (inside diameter 9 mm, column length 150 mm) equipped at each end with a filter with a pore diameter of 15 μm was uniformly packed with an agarose material (Biogel A-5m, particle size 50 to 100 mesh, product of Bio-Rad Laboratories, Inc.), a vinylic polymer material (TOYOPEARL HW-65, particle diameter 50 to 100 μm, product of Tosoh Corporation) or a cellulosic material (Cellulofine GC-700m, particle diameter 45 to 105 μm, product of Chisso Corporation). Water was passed through each column by means of a peristaltic pump, and the relation between flow rate and pressure loss ($\Delta P$) was determined. The results thus obtained are shown in FIG. 3.

Figure 3:
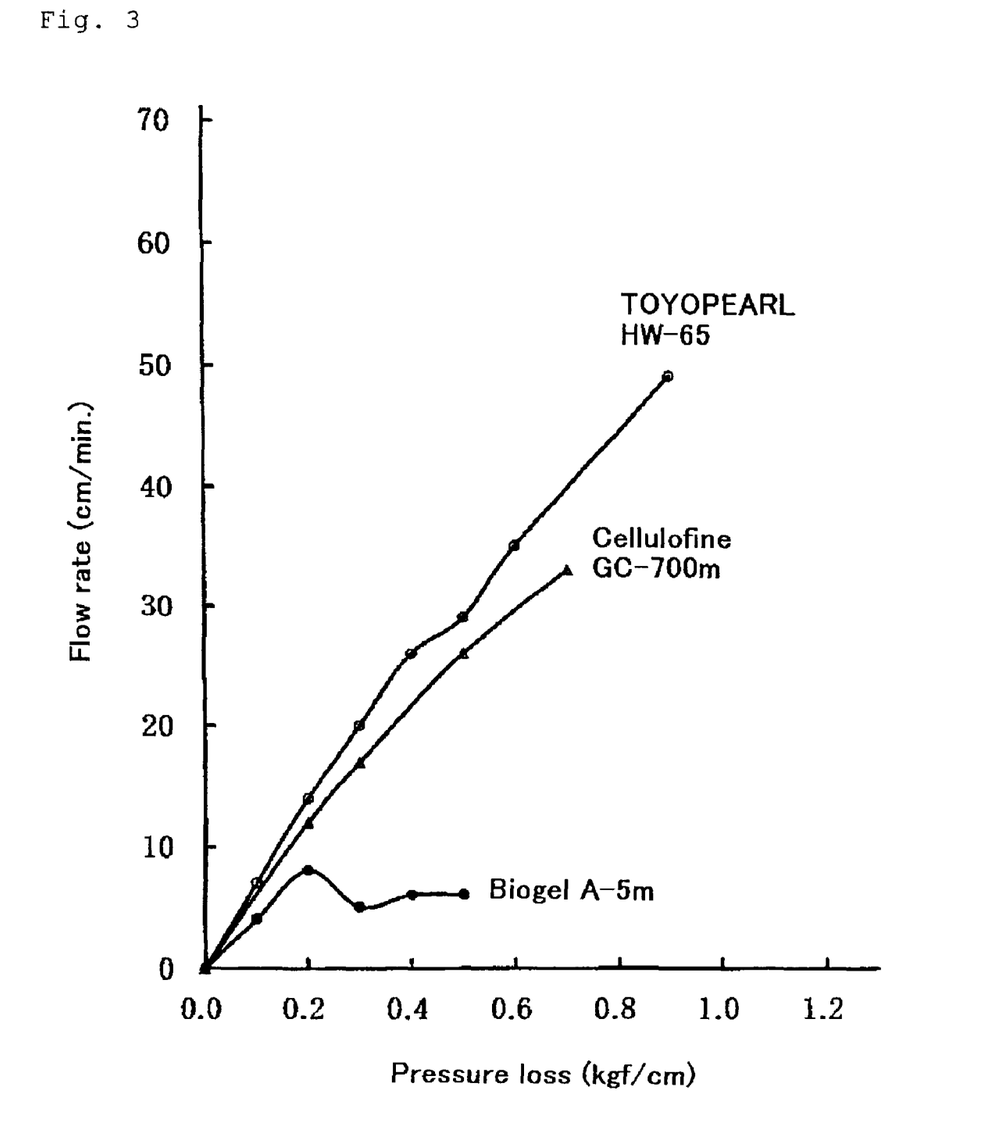
FIG. 3 This figure shows the relation between flow rate and pressure loss.

As shown in FIG. 3, it is seen that the flow rate increased approximately in proportion to the increase in pressure with TOYOPEARL HW-65 and Cellulofine GC-700m whereas, in the case of Biogel A-5m, compaction was induced and the flow rate did not increase even when the pressure was increased. In the present invention, an adsorbent showing a linear relationship between pressure loss ($\Delta P$) and flow rate until a pressure of 0.3 kgf/cm$^2$ is referred to as a hard adsorbent.

Production Example

Water was added to a mixture of 24 L of porous cellulose beads with an average particle diameter of about 446 μm, a coefficient of variance in particle diameter distribution of 14% and an exclusion limit of molecular weight for spherical proteins of 5×10$^7$, 6.6 L of a 4 N aqueous NaOH solution and 7 L of epichlorohydrin to make the whole amount 33 L, and the reaction was allowed to proceed with stirring at 40° C. for 2 hours. Thereafter, the beads were thoroughly washed with water to give epoxidized cellulose beads. The epoxy group content in the epoxidized cellulose beads was 16.4 μmol/mL (wet volume).

An aqueous solution of dextran sulfate was prepared by dissolving 3 kg of dextran sulfate (sulfur content about 18%, molecular weight about 4,000) in 15 L of water, 24 L of the epoxidized cellulose beads in the state wetted with water was added, the mixture was made alkaline with an aqueous solution of NaOH, and the reaction was allowed to proceed at 45° C. for 6 hours. Thereafter, the beads were thoroughly washed with water and saline, a solution prepared by dissolving 0.34 kg of L-tryptophan in 11 L of a dilute aqueous solution of NaOH was added, and the reaction was allowed to proceed at 50° C. for 8 hours. The beads were then thoroughly washed with water and saline to give an adsorbent consisting of dextran sulfate- and tryptophan-immobilized cellulose beads. This adsorbent had an average particle diameter of 446 μm; the coefficient of variance in particle diameter distribution was 14%. The average particle diameter and coefficient of variance in particle diameter distribution were determined by taking an appropriate amount of a slurry of the water-insoluble carrier or adsorbent after thorough stirring into a dish, obtaining an enlarged photograph with adsorbent particles not smaller than about 150 μm being focused upon using a stereomicroscope, and measuring 100 adsorbent particles on the photograph by the three point circle method, followed by calculation on the number basis.

Example 1

An adsorber was obtained by packing the adsorbent of the Production Example in an acrylic column (2.7 mL in capacity) having an inside diameter of 10 mm and a length of 34 mm and equipped with a polyethylene terephthalate mesh 150 μm in opening size at each end. Then, 40 mL of the blood of a normal subject as supplemented with 5 units, per mL of blood, of heparin for preventing coagulation was circulated through the adsorber at a flow rate of 6.5 mL/min for 2 hours. The cytometric data concerning the pooled blood samples before and after 2 hours of circulation were as shown in Table 1; each hemocyte species showed a good passing behavior. The LDL-cholesterol, fibrinogen and HDL-cholesterol contents in the pooled blood samples before and after circulation were as shown in Table 2. The LDL-cholesterol content lowered from 163 mg/dL to 105 mg/dL and the fibrinogen content from 210 mg/dL to 152 mg/dL, while the HDL-cholesterol content lowered only slightly from 49 mg/dL to 46 mg/dL.

The amount of tryptophan immobilized on the adsorbent of the Production Example was determined based on the nitrogen content of the adsorbent. Thus, 1 mL of the adsorbent of the Production Example was thoroughly washed with water, then dried under reduced pressure at 60° C. for 6 hours or longer and assayed using a total nitrogen microanalyzer. As a result, the adsorbent of the Production Example had an immobilized tryptophan content of 7.8 μmol/mL.

The amount of dextran sulfate immobilized on the adsorbent of the Production Example was determined utilizing the affinity of dextran sulfate for toluidine blue. Thus, about 100 mL of an aqueous solution of toluidine blue (Basic Blue 17 (TOKYO CHEMICAL INDUSTRY CO., LTD.)) adjusted to about 90 mg/L was added to 3 mL of the adsorbent of the Production Example, the mixture was stirred for 10 minutes and then allowed to stand, the toluidine blue concentration in the supernatant was determined based on the absorbance at 630 nm, and the amount in question was calculated based on the decrease in dye content. The adsorbent of the Production Example had an immobilized dextran sulfate content of 0.23 μmol/mL.

TABLE 1

| | Average particle diameter [μm] | Amount of immobilized polyanion compound [μmol/ml] | Amount of immobilized tryptophan [μmol/ml] | Number of leukocyte [×10²/μl] | | After blood passage/ before blood passage × 100[%] | Number of platelet [×10⁴/μl] | | After blood passage/ before blood passage × 100[%] | Number of hemocyte [×10⁴/μl] | | After blood passage/ before blood passage × 100 [%] |
|---|---|---|---|---|---|---|---|---|---|---|---|---|
| | | | | Before blood passage | After blood passage | | Before blood passage | After blood passage | | Before blood passage | After blood passage | |
| Example 1 | 446 | 0.23 | 7.8 | 59 | 45 | 76 | 22.7 | 17.3 | 76 | 498 | 502 | 101 |

TABLE 2

| | Average particle diameter [μm] | Amount of immobilized polyanion compound [μmol/ml] | Amount of immobilized tryptophan [μmol/ml] | LDL-cholesterol [mg/dl] | | Proportion of decrease [%] | Fibrinogen [mg/dl] | | Proportion of decrease [%] |
|---|---|---|---|---|---|---|---|---|---|
| | | | | Before blood passage | After blood passage | | Before blood passage | After blood passage | |
| Example 1 | 446 | 0.23 | 7.8 | 163 | 105 | 36 | 210 | 152 | 28 |

| | HDL-cholesterol [mg/dl] | | Proportion of decrease [%] | Adsorption | | |
|---|---|---|---|---|---|---|
| | Before blood passage | After blood passage | | LDL-cholesterol [mg/mL-gel] | Fibrinogen [mg/mL-gel] | HDL-cholesterol [mg/mL-gel] |
| Example 1 | 49 | 46 | 6 | 4.7 | 5.1 | 0.2 |

Example 2

The adsorbent of the Production Example (slurry concentration 30%, liquid amount 16 L) was dispersed in a vessel equipped with a mesh having an opening size of 212 μm, and the slurry solvent (water) was circulated from the section separated by the mesh and free of the adsorbent to the vessel via a nozzle in a circulation line at a flow rate of 32 L/min for 10 minutes while the adsorbent was always maintained in a dispersed state. The slurry solvent circulating line outside the vessel equipped with the mesh had a mesh with an opening size of 104 μm, and the amount of the adsorbent that had flown out of the 212-μm mesh and had been caught by the 104-μm mesh during the above-mentioned 10 minutes of circulation was determined. That amount was 8.0 mL, as shown in Table 3.

TABLE 3

| | Mesh opening size of adsorber [μm] | Mesh opening size of microparticle-removing vessel [μm] | Mesh opening size of microparticle-removing vessel/mesh opening size of adsorber [-] | Concentration of microparticle-removed slurry [%] | Amount of microparticle-removed slurry [L] | Amount of adsorbent of 100 μm or more, flowed out from mesh of microparticle-removing vessel [mL] |
|---|---|---|---|---|---|---|
| Example 2 | 150 | 212 | 1.41 | 30 | 16 | 8 |
| Comparative Example 1 | 150 | 233 | 1.55 | 30 | 16 | 20 |

Even when it is supposed that the circulation line is equipped with a 0.22-μm filter for capturing water-insoluble microparticles in place of the 104-μm mesh and water-insoluble microparticles are removed under the above conditions, the adsorbent loss (flowing out) resulting from the removal of water-insoluble microparticles is estimated to be about 8.0 mL; this amount is small. At this level of flowing out, the filter clogging due to flowing-out water-insoluble microparticles on the occasion of continuous operation can be avoided by providing a prefilter before the filter for capturing water-insoluble microparticles.

When the same adsorber mesh opening size as that in Example 1 is employed and the mesh opening size of the vessel for removing water-insoluble microparticles is the same as in this example, the ratio between the mesh opening size (212 μm) for removing water-insoluble microparticles and the adsorber mesh opening size (150 μm) is 1.41.

Comparative Example 1

The adsorbent of the Production Example (slurry concentration 30%, liquid amount 16 L) was dispersed in a vessel equipped with a mesh having an opening size of 233 μm, and the slurry solvent (water) was circulated from the section separated by the mesh and free of the adsorbent to the vessel via a nozzle in a circulation line at a flow rate of 32 L/min for 10 minutes while the adsorbent was always maintained in a dispersed state. The slurry solvent circulating line outside the vessel equipped with the mesh had a mesh with an opening size of 104 μm, and the amount of the adsorbent that had flown out of the 233-μm mesh and had been caught by the 104-μm mesh during the above-mentioned 10 minutes of circulation was determined. That amount was 20 mL, as shown in Table 3.

Even when it is supposed that the circulation line is equipped with a 0.22-μm filter for capturing water-insoluble microparticles in place of the 104-μm mesh and water-insoluble microparticles are removed under the above conditions, the adsorbent loss (flowing out) resulting from the removal of water-insoluble microparticles is estimated to be about 20 mL; this amount is greater than that of Example 2. Even if a prefilter is disposed for avoiding the clogging of the filter for removing water-insoluble microparticles on the occasion of continuous operation, the prefilter size becomes greater as compared with Example 2.

When the same adsorber mesh opening size as that in Example 1 is employed and the mesh opening size of the vessel for removing water-insoluble microparticles is the same as in this example, the ratio between the mesh opening size (233 μm) for removing water-insoluble microparticles and the adsorber mesh opening size (150 μm) is 1.55.

The adsorbent of the Production Example (slurry concentration 15%, liquid amount 16 L) was dispersed in a washing liquid in a microparticle-removing vessel equipped with a mesh having an opening size of 212 μm, and the washing liquid was circulated from the section separated by the mesh and free of the adsorbent to the microparticle-removing vessel via a nozzle in a circulating and water-insoluble microparticle-removing line having a 0.22-μm filter for capturing water-insoluble microparticles flowing out through the 212-μm mesh at a flow rate of 32 L/min for 10 minutes while the adsorbent in the microparticle-removing vessel was always maintained in a dispersed state. The ratio between the mesh opening size (212 μm) for removing water-soluble microparticles and the adsorber mesh opening size (150 μm) is 1.41.

The adsorbent (about 250 mL) having water-insoluble microparticles removed therefrom was packed in each of 6 columns having a capacity of 250 mL and equipped with the same adsorber meshes as used in Example 1, in a closed system, and then water filtered through a 0.22-μm filter was passed through each adsorber to allow the same to release microparticles, and water-insoluble microparticles from each adsorber were counted. (Since the adsorber mesh opening size was 150 μm, the upper limit to the particle diameters of water-insoluble microparticles was 150 μm.) As regards the method of measurement of water-insoluble microparticles, the method of testing for water-insoluble microparticles as prescribed in the Japanese Pharmacopoeia, 14th Revised Edition, General Rules for Preparations, 17: Injections is not applicable since the cellulosic adsorbent material was semi-transparent. Therefore, water-insoluble microparticles were measured using a Coulter counter measuring the equivolume sphere equivalent diameter of a particle passing through an aperture by detecting the electric resistance on the occasion of the passage. Since, however, the adsorbent-constituting water-insoluble carrier was porous, the value obtained by multiplying each particle diameter measured by the Coulter counter by a correction factor was regarded as the real particle diameter (real particle diameter=measured particle diameter×2). (In the subsequent examples and comparative example, the numbers of water-insoluble microparticles were determined by this measurement method.) The results of measurements of the numbers of water-insoluble microparticles were such that the mean of the measured values of water-insoluble microparticles not smaller than 10 μm but not larger than 150 μm for the 6 adsorbers+6SD was 8474 per adsorber and the mean of the measured values of water-insoluble microparticles not smaller than 25 μm but not larger than 150 μm for the 6 adsorbers+6SD was 1648 per adsorber, as shown in Table 4. Thus, the numbers of water-insoluble microparticles had arrived at the safety levels.

Example 4

The adsorbent of the Production Example (slurry concentration 30%, liquid amount 16 L) was dispersed in a washing liquid in a microparticle-removing vessel equipped with a mesh having an opening size of 212 μm, and the washing liquid was circulated from the section separated by the mesh and free of the adsorbent to the microparticle-removing vessel via a nozzle in a circulating and water-insoluble microparticle-removing line having a 0.22-μm filter for capturing water-insoluble microparticles flowing out through the 212-μm mesh at a flow rate of 32 L/min for 10 minutes while the adsorbent in the microparticle-removing vessel was always maintained in a dispersed state. The ratio between the mesh opening size (212 μm) for removing water-soluble microparticles and the adsorber mesh opening size (150 μm) is 1.41.

The adsorbent (about 250 mL) having water-insoluble microparticles removed therefrom was packed in each of 6 columns having a capacity of 250 mL and equipped with the same adsorber meshes as used in Example 1, in a closed system, and then water filtered through a 0.22-μm filter was passed through each adsorber to allow the same to release microparticles, and water-insoluble microparticles from each adsorber were counted. (Since the adsorber mesh opening size was 150 μm, the upper limit to the particle diameters of water-insoluble microparticles was 150 μm.) The results of measurements of the numbers of water-insoluble microparticles were such that the mean of the measured values of water-insoluble microparticles not smaller than 10 μm but not larger than 150 μm for the 6 adsorbers+6SD was 8501 per adsorber and the mean of the measured values of water-insoluble microparticles not smaller than 25 μm but not larger than 150 μm for the 6 adsorbers+6SD was 1652 per adsorber, as shown in Table 4. Thus, the numbers of water-insoluble microparticles had arrived at the safety levels.

Example 5

The adsorbent of the Production Example (slurry concentration 50%, liquid amount 16 L) was dispersed in a washing liquid in a microparticle-removing vessel equipped with a mesh having an opening size of 212 μm, and the washing liquid was circulated from the section separated by the mesh and free of the adsorbent to the microparticle-removing vessel via a nozzle in a circulating and water-insoluble microparticle-removing line having a 0.22-μm filter for capturing water-insoluble microparticles flowing out through the 212-μm mesh at a flow rate of 32 L/min for 10 minutes while the adsorbent in the microparticle-removing vessel was always maintained in a dispersed state. The ratio between the mesh opening size (212 μm) for removing water-soluble microparticles and the adsorber mesh opening size (150 μm) is 1.41.

The adsorbent (about 250 mL) having water-insoluble microparticles removed therefrom was packed in each of 6 columns having a capacity of 250 mL and equipped with the same adsorber meshes as used in Example 1, in a closed system, and then water filtered through a 0.22-μm filter was passed through each adsorber to allow the same to release microparticles, and water-insoluble microparticles from each adsorber were counted. (Since the adsorber mesh opening size was 150 μm, the upper limit to the particle diameters of water-insoluble microparticles was 150 μm.) The results of measurements of the numbers of water-insoluble microparticles were such that the mean of the measured values of water-insoluble microparticles not smaller than 10 μm but not larger than 150 μm for the 6 adsorbers+6SD was 4412 per adsorber and the mean of the measured values of water-insoluble microparticles not smaller than 25 μm but not larger than 150 μm for the 6 adsorbers+6SD was 831 per adsorber, as shown in Table 4. Thus, the numbers of water-insoluble microparticles had arrived at the safety levels.

Comparative Example 2

The adsorbent of the Production Example (slurry concentration 30%, liquid amount 16 L) was dispersed in a washing liquid in a microparticle-removing vessel equipped with a mesh having an opening size of 180 μm, and the washing liquid was circulated from the section separated by the mesh and free of the adsorbent to the microparticle-removing vessel via a nozzle in a circulating and water-insoluble microparticle-removing line having a 0.22-μm filter for capturing water-insoluble microparticles flowing out through the 180-μm mesh at a flow rate of 32 L/min for 10 minutes while the adsorbent in the microparticle-removing vessel was always maintained in a dispersed state. The ratio between the mesh opening size (180 μm) for removing water-soluble microparticles and the adsorber mesh opening size (150 μm) is 1.20.

The adsorbent (about 250 mL) having water-insoluble microparticles removed therefrom was packed in each of 6 columns having a capacity of 250 mL and equipped with the same adsorber meshes as used in Example 1, in a closed system, and then water filtered through a 0.22-μm filter was passed through each adsorber to allow the same to release microparticles, and water-insoluble microparticles from each adsorber were counted. (Since the adsorber mesh opening size was 150 μm, the upper limit to the particle diameters of water-insoluble microparticles was 150 μm.) The results of measurements of the numbers of water-insoluble microparticles were such that the mean of the measured values of water-insoluble microparticles not smaller than 10 μm but not larger than 150 μm for the 6 adsorbers+6SD was 23909 per adsorber and the mean of the measured values of water-insoluble microparticles not smaller than 25 μm but not larger than 150 μm for the 6 adsorbers+6SD was 13142 per adsorber, as shown in Table 4. Thus, the numbers of water-insoluble microparticles had not arrived at the safety levels.

TABLE 4

|  | Mesh opening size of adsorber [μm] | Mesh opening size of microparticle-removing vessel [μm] | Mesh opening size of microparticle-removing vessel/ mesh opening size of adsorber [-] | Concentration of microparticle-removed slurry [%] | Amount of microparticle-removed slurry [L] | Mean of measured value of water-insoluble microparticles of 10-150 μm + 6SD (per adsorber) | Mean of measured value of water-insoluble microparticles of 25-150 μm + 6SD (per adsorber) |
|---|---|---|---|---|---|---|---|
| Example 3 | 150 | 212 | 1.41 | 15 | 16 | 8474 | 1648 |
| Example 4 | 150 | 212 | 1.41 | 30 | 16 | 8501 | 1652 |
| Example 5 | 150 | 212 | 1.41 | 50 | 16 | 4412 | 831 |
| Comparative Example 2 | 150 | 180 | 1.20 | 30 | 16 | 23909 | 13142 |

INDUSTRIAL APPLICABILITY

In accordance with the invention, it is now possible to obtain direct hemoperfusion adsorbers packed with an adsorbent made by using a water-insoluble carrier having a relatively readily available particle size distribution, with water-insoluble microparticles having been removed therefrom to a therapeutically safe level, without needing any special granulation apparatus for producing an adsorbent uniform in particle diameter distribution from which water-insoluble microparticles can be readily removed or without need of any coating treatment for inhibiting the release of water-insoluble microparticles. In accordance with the invention, it is also possible to obtain direct hemoperfusion adsorbers with ease and increase the safety against water-insoluble microparticles on the occasion of treatment by using the same.

The invention claimed is:

1. A method of obtaining adsorbents for packing in direct hemoperfusion adsorbers
    which comprises removing water-insoluble microparticles from an adsorbent comprising a group of particles having a number average particle diameter of not smaller than 300 μm but not greater than 600 μm, with the coefficient of variation in particle diameter distribution being not lower than 10% but not higher than 20%, by using a mesh such that the ratio of the mesh opening size for removing water-insoluble microparticles to the mesh opening size of the adsorber is not lower than 1.3 but not higher than 1.5,
    wherein the mesh opening size of the adsorber is not smaller than 100 μm but not larger than 200 μm.

* * * * *